US011283935B2

(12) United States Patent
Singhal et al.

(10) Patent No.: US 11,283,935 B2
(45) Date of Patent: Mar. 22, 2022

(54) CONFIGURABLE CIRCUIT TELEMETRY SYSTEM

(71) Applicant: TEXAS INSTRUMENTS INCORPORATED, Dallas, TX (US)

(72) Inventors: Shobhit Singhal, Bangalore (IN); Vikas Lakhanpal, Bengaluru (IN); Preetam Tadeparthy, Bengaluru (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 0 days.

(21) Appl. No.: 16/730,776

(22) Filed: Dec. 30, 2019

(65) Prior Publication Data
US 2021/0203786 A1    Jul. 1, 2021

(51) Int. Cl.
*H04M 11/02*     (2006.01)
*H04M 11/00*     (2006.01)
*G01R 19/12*     (2006.01)
*G06F 9/38*       (2018.01)
*A61N 1/372*     (2006.01)

(52) U.S. Cl.
CPC ....... *H04M 11/002* (2013.01); *A61N 1/37252* (2013.01); *G01R 19/12* (2013.01); *G06F 9/3877* (2013.01)

(58) Field of Classification Search
USPC .... 379/106.03, 106.01, 106.08, 93.05, 93.09
See application file for complete search history.

(56) References Cited

U.S. PATENT DOCUMENTS

| | | | | | |
|---|---|---|---|---|---|
| 3,617,639 | A | * | 11/1971 | Propper | H04M 11/002 379/32.01 |
| 6,034,623 | A | * | 3/2000 | Wandel | H04Q 9/00 340/870.01 |
| 6,038,297 | A | * | 3/2000 | Garland | H04M 11/002 379/106.01 |
| 6,163,602 | A | * | 12/2000 | Hammond | G01D 4/004 379/106.01 |
| 6,263,055 | B1 | * | 7/2001 | Garland | H04M 11/02 379/102.01 |

(Continued)

OTHER PUBLICATIONS

International Search Report and Written Opinion dated Mar. 30, 2021, PCT Application No. PCT/US2020/066373, 7 pages.

*Primary Examiner* — Maria El-Zoobi
(74) *Attorney, Agent, or Firm* — Michelle F. Murray; Charles A. Brill; Frank D. Cimino

(57) ABSTRACT

Aspects of the disclosure provide for a circuit, in some examples, including a storage element, a co-processor, and a telemetry sequencer coupled to the storage element and the co-processor. The telemetry sequencer is configured to implement a digital state machine to receive configuration information indicating a type of telemetry data for generation, retrieve operations and operands, where the operations and the operands define a sequential series of actions for execution to generate the telemetry data, drive the co-processor with the operations and the operands by passing some of the operations and some of the operands to the co-processor for processing by the co-processor, receive, from the co-processor, and store an intermediate output of the series of actions as the telemetry data in a first format, and receive, from the co-processor, and store a final output of the series of actions as the telemetry data in a second format.

18 Claims, 3 Drawing Sheets

(56) References Cited

U.S. PATENT DOCUMENTS

| | | | | |
|---|---|---|---|---|
| 6,334,060 B1* | 12/2001 | Sham | ............... | G08C 17/02 |
| | | | | 331/4 |
| 6,487,252 B1* | 11/2002 | Kleider | ............ | H04L 5/0048 |
| | | | | 370/320 |
| 6,674,764 B1* | 1/2004 | Garland | ............ | H04M 11/002 |
| | | | | 370/449 |
| 7,304,587 B2* | 12/2007 | Boaz | ............... | H04Q 9/00 |
| | | | | 340/870.02 |
| 7,653,186 B2* | 1/2010 | Hosain | ............ | H04M 11/002 |
| | | | | 379/106.01 |
| 8,270,910 B2* | 9/2012 | Picard | ............ | H04W 40/22 |
| | | | | 455/69 |
| 8,607,305 B2* | 12/2013 | Neystadt | ............ | G06F 21/44 |
| | | | | 726/1 |
| 8,710,810 B1* | 4/2014 | McJimsey | ............ | H02M 3/157 |
| | | | | 323/272 |
| 9,639,134 B2 | 5/2017 | Gendler | | |
| 2015/0162827 A1 | 6/2015 | Tang et al. | | |

\* cited by examiner

CONFIGURABLE CIRCUIT TELEMETRY SYSTEM

BACKGROUND

Telemetry relates to the measurement, reporting, and/or collection of data for the monitoring of systems. In electronic systems, telemetry data can include measurements of voltage, current, temperature, power, or any other metric or value that may be of interest or benefit in monitoring the electronic systems. As a quantity of telemetry data increases, such as when a greater number of metrics are monitored, difficulty can arise in efficiently generating and/or processing the telemetry data.

SUMMARY

At least some aspects of the present disclosure provide for a circuit. In at least one example, the circuit includes a storage element, a co-processor, and a telemetry sequencer coupled to the storage element and the co-processor. The telemetry sequencer is configured to implement a digital state machine to receive configuration information indicating a type of telemetry data for generation and retrieve operations and operands associated with the type of the telemetry data for generation from the storage element. The operations and the operands define a sequential series of actions for execution to generate the telemetry data. The telemetry system is further configured to implement the digital state machine to drive the co-processor with the operations and the operands associated with the type of the telemetry data for generation by passing at least some of the operations and at least some of the operands to the co-processor for processing by the co-processor. The telemetry system is further configured to digital state machine receive, from the co-processor, and store an intermediate output of the series of actions as the telemetry data in a first format. The telemetry system is further configured to digital state machine receive, from the co-processor, and store a final output of the series of actions as the telemetry data in a second format.

Other aspects of the present disclosure provide for a system. In at least some examples, the system includes a multi-phase power supply, a central processing unit, and a telemetry system coupled to the multi-phase power supply and the central processing unit. The telemetry system is configured to implement a digital state machine to receive sensor data in a digital format indicating a measurement of a condition of the system. The telemetry system is further configured to load plurality of operations and a plurality of operands that together define a series of actions for determining telemetry data utilizing the sensor data as one of the operands. The telemetry system is further configured to implement the digital state machine to execute the series of actions to generate a final output that is a result of a last operation of the series of actions and store the final output as the telemetry data in a first format. The system is configured to modify a value of a signal output by the multi-phase power supply based at least partially on the generated final output.

Other aspects of the present disclosure provide for a method implemented by a digital state machine. In at least some examples, the method comprises receiving sensor data in a digital format indicating a condition of a circuit and loading a series of actions for determining telemetry data utilizing the sensor data as an operand. The series of actions is defined according to a plurality of operations and a plurality of operands. Loading the series of actions comprises loading the plurality of operations into a telemetry sequence slot for calculation by a co-processor and loading the plurality of operands into the telemetry sequence slot for calculation by the co-processor. The method further comprises executing the series of actions to generate a final output that is a result of a last operation of the series of actions. Executing the series of actions comprises passing at least some of the plurality of operations and at least some of the plurality of operands to the co-processor for processing by the co-processor. The method further includes storing the final series of actions output as the telemetry data in a first format.

BRIEF DESCRIPTION OF THE DRAWINGS

For a detailed description of various examples, reference will now be made to the accompanying drawings in which.

DETAILED DESCRIPTION

Figure 1:
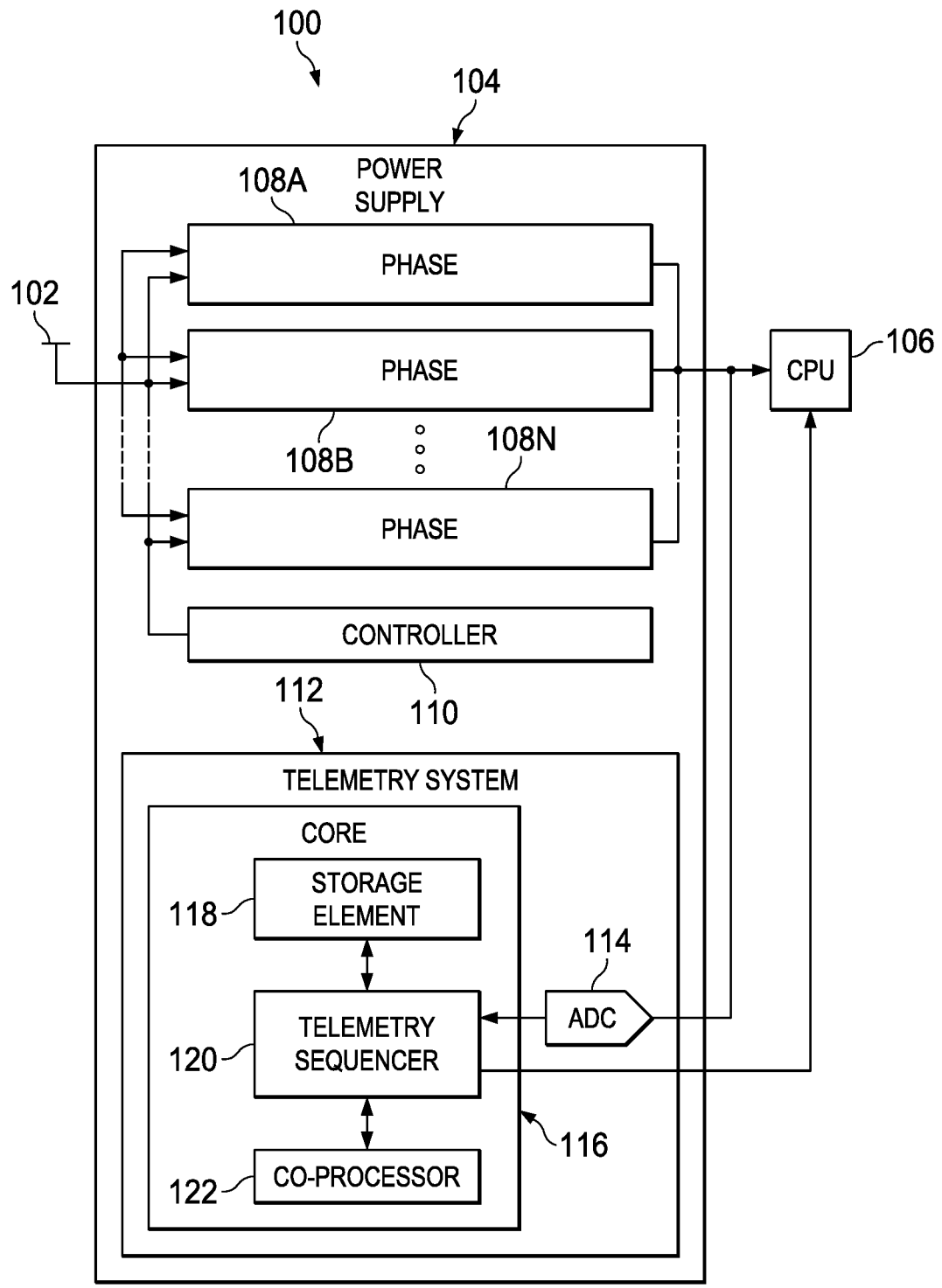
FIG. 1 shows a block diagram of an illustrative server system in accordance with various examples.

Some approaches to providing telemetry data include hardware solutions that are customized to some degree for either a specific customer's application or for a specific measurement. For example, hardware specific to a certain parameter such as voltage, current, temperature, etc. generates telemetry data for that certain parameter. Some examples of the hardware are further specific to a certain format, such as complying with a particular standard, having a particular scale, having a custom format defined by a customer, etc. In a system in which multiple metrics are monitored to generate the telemetry data, including individual hardware solutions for each desired format, measurement, or other criteria can result in increased space and/or power consumed by telemetry circuitry. One such system is a multi-phase direct current (DC) to DC (DC-DC) power converter.

In at least some implementations of DC-DC power converters, a plurality of parameters are monitored to generate telemetry data. This telemetry data is used, in some examples, internally in the DC-DC power converter, such as for control. In other examples, the telemetry data is used outside of the DC-DC power converter and/or the circuit generating the telemetry data. In other systems, more or fewer parameters may be monitored to generate the telemetry data. The monitored data may be reportable in various formats. For example, the monitored data may be processed and reported in an integer format, a full-precision format, a half-precision format, a linear format, a percentage format, a power management bus (PMBUS) format, a serial voltage identification (VID) (SVID) format, a SVID interface (SVI) format, a parallel VID (PVID) format, an adaptive voltage scaling (AVS) format, an I2C format, a custom format, etc. In some examples, data processed from a raw format (e.g., as measured and output by a sensor or as converted to a digital domain from an analog domain in which the data was measured) may be desired in multiple formats. For example, a customer may wish for the data to be reported in a first format and a second format, where the second format is a different than the first format. The same data may be needed by a telemetry system in yet a third format for use in a calculation. For example, a customer may wish for an output current to be reported in milliamperes (mA) scale and reported as a percentage of maximum output current. The output current may then be further needed by the telemetry system in amperes (A) scale for use in determining output power. In a telemetry system in which each of these formats is generated by specific hardware solutions, three separate circuits may be required. For example, the telemetry system might include a circuit to determine output current in mA, a circuit to determine output current in A, and a circuit for determining output current as a percentage of maximum output current.

In modern server systems, and particularly server systems that are high performance, many different criteria may be monitored and at least some of those criteria may be reported and/or used by the server system in multiple formats. In at least some examples, such high performance systems include at least systems that utilize a power supply and may tune performance of a processing unit (e.g., a central processing unit (CPU)) based on telemetry data pertaining to that power supply. The formats in which telemetry data is requested may change from time to time, such as late in a development cycle of a telemetry system or during the life cycle of the telemetry system. For example, a telemetry system may be rendered obsolete shortly after being launched if the telemetry system performs measurements with specific hardware circuits, as discussed above, and does not include hardware circuits specific to new format requirements. In this regard, it may be desirable for a telemetry system to be configurable to provide telemetry data in a manner largely uncoupled from the hardware that generates the telemetry data. For example, such that the telemetry system generates telemetry data using a same hardware circuit to generate a plurality of telemetry data parameters (e.g., voltage, current, power, temperature, efficiency, etc.) and in a plurality of formats. Additionally, in some examples a telemetry system may have a capability to provide telemetry data that is not of interest to a particular customer, or is not of interest at a particular time, and thus the generation of which at a particular time may not be an efficient use of resources. However, that telemetry system may operate in a sequential manner such that it nonetheless generates and outputs that telemetry data resulting in reduced processing efficiency and increased delay. Therefore, it may be further desirable for a telemetry system to include configurability in which operations are performed and/or which telemetry data is generated, such as in a non-sequential manner, rather than being limited to operation in a sequential manner.

To implement such functionality using specific hardware solutions would result in a significantly large number of circuits. At least some of the circuits might be largely redundant or may be unused by some customers, resulting in increased circuit size and cost. Despite the large number of circuits, for some customers, desired functionality might still be missing when that desired functionality is highly customized to the particular customer. To provide customization, some telemetry systems might utilize a microcontroller or other form of CPU to generate telemetry data. However, telemetry data is often rapidly changing and may have comparatively short time periods for generation, reporting, and for action to be taken based on the telemetry data to prevent damage to a component being monitored to generate the telemetry data. For example, some implementations may require telemetry data to be generated and reported in less than about one microsecond. In a microcontroller or CPU that could provide the configurability that specific hardware solutions lack, the microcontroller or CPU, especially when utilizing floating point arithmetic, may be incapable of meeting the timing requirements for telemetry data generation and reporting. Furthermore, the generation and reporting of telemetry data is an ongoing process, in many implementations continuing for a duration of time that a system being monitored is powered on. To have a microcontroller or CPU of that system generating the telemetry data would prevent that microcontroller or CPU from having capacity to perform other processing, limiting performance of the system.

At least some aspects of the present disclosure provide for a telemetry system. The telemetry system, in some examples, includes multiple points of configurability. For example, the telemetry system includes pipelined operations that are time-multiplexed into telemetry sequence slots, where slots are executed sequentially. However, unlike the hardware specific solutions discussed above, the configurability of the telemetry system enables operations to be omitted from the telemetry sequence slots. Operations may be omitted, for example, when the operations correspond to telemetry data not of interest to a customer or not needed at a particular time (e.g., such as during startup). The telemetry system is further configurable in operations performed on sensor data. For example, whereas the hardware solutions discussed above are specific to a particular series of actions to generate the telemetry data and a particular format, the telemetry system provided for herein is dynamic. Dynamic, as used herein, may indicate that telemetry sequence slotting may be changed based on a desired operation mode. Dynamic may further indicate that operands may be changed in the series of actions. For example, a changing operand, such as temperature, may be changed in series of actions that utilize temperature as an operand, rather than relying on pre-coded data. Further, the dynamic nature of the telemetry sequence slotting may permit different operands to be selected based one or more results of series of actions that generate telemetry data or of measured or sensed data. For example, a given operand may have a first value under certain conditions (e.g., such as when measured temperature exceeds a threshold) and a second value under other conditions (e.g., such as when measured temperature does not exceed the threshold). In at least some implementations, a telemetry sequencer implements a digital state machine that performs a plurality of actions to generate the telemetry data using a same hardware set, such as a co-processor. In at least some examples, the co-processor is an arithmetic logic unit (ALU) or other component capable of performing mathematical calculations and/or logical operations to aid the telemetry sequencer in generating the telemetry data.

In some examples, the series of actions include one or more mathematical operations, each accepting at least two operands. In some examples, the mathematical operations are cascaded such that the telemetry system provides one or more taps, or intermediate/additional outputs, prior to a final mathematical operation of the series of actions. For example, in a generation of output current telemetry data in mA, the telemetry system may provide a tap prior to the series of actions converting the output current from A to mA. In this way, the output current in A may be stored by the telemetry system to be used in subsequent calculations (such as power in units of Watts) while also providing the output current in mA using the same hardware and at substantially a same time. Furthermore, the configurability, and programmability, of the telemetry system enables series of actions for generating telemetry data in a desired type or format to be added at will by a customer. For example, if at a time of manufacturing of the telemetry system it is not known that a specific type of telemetry data may be desired at a later date, and yet the specific type of telemetry data becomes desired, the telemetry system is programmable to provide that telemetry data. In contrast, the specific hardware solutions discussed above would lack the hardware configuration and components necessary to provide the new specific type of telemetry data that is providable by the telemetry system of the present disclosure.

At least some implementations of the telemetry system of the present disclosure improve over specific hardware solutions that generate telemetry data by providing programmability and configurability to generate a particular telemetry data at a particular time using a same hardware component as generates another telemetry data at another time. This programmability enables the telemetry system of the present disclosure to have different telemetry data generation sequences during startup, post-startup, when a fault is detected, during calibration, etc. This improves over the specific hardware solutions that follow a specific order of telemetry data generation regardless of whether or not the generated telemetry data is of use or desired at a given time, thereby wasting resources and time. The telemetry system of the present disclosure also improves over specific hardware solutions that generate telemetry data by enabling both intermediate and final results of a series of actions for generating telemetry data to be output, thereby reducing redundant processing and saving time when compared to the specific hardware solutions that generate one type of telemetry data and in one format per hardware solution. The telemetry system of the present disclosure further improves over specific hardware solutions that generate telemetry data by providing post-manufacturing configurability to enable support for the generation of new telemetry data, or telemetry data in a new format, that the specific hardware solutions would be incapable of performing because of its hardware nature.

A device implementing the telemetry system of the present disclosure instead of specific hardware solutions or CPUs that generate telemetry data is improved by being able to more rapidly provide telemetry data, at lower power consumption, for a component that consumes less area. Particularly, at least some implementations of the telemetry system of the present disclosure have a die size approximately 2 square millimeters less than a specific hardware solution for generating a given type of telemetry data (e.g., current in one or more formats). For example, the telemetry system of the present disclosure may consume approximately 1.15 square millimeters of die space compared to a hardware specific solution that consumes approximately 3.2 square millimeters of die space. The reduction in die surface area results in reduced cost of manufacturing of the telemetry system of the present disclosure and a reduced bill of materials (e.g., components required) in the telemetry system of the present disclosure, further reducing a cost of the telemetry system of the present disclosure.

Turning now to FIG. 1, an illustrative server system 100 is shown. While described as a server system, the system 100 may be representative of implementations of other systems. For example, the system 100 may be generally representative of other systems in which a multi-phase power supply is implemented and monitored or any system in which telemetry data is measured. In at least one example, the system 100 includes a power source 102, a power supply 104, and a CPU 106. The power source 102 is, for example, mains power or power received from an adapter that converts mains power from alternating current (AC) to DC. In other examples, the power source 102 is a battery or other power storage device. The power supply is 104, in some examples, a component that receives power from the power source 102 and generates one or more supply signals for supplying the CPU 106 with power. While only one coupling is shown between the power supply 104 and the CPU 106, in various examples any number of couplings may be present. Additionally, the system 100 may include one or more additional components (not shown) that also receive one or more supply signals from the power supply 104.

In at least one example, the power supply 104 is a multi-phase power supply. For example, the power supply 104 includes a plurality of phases 108A, 108B, ... 108N that are selectively controlled by a multi-phase controller 110 to be active, or inactive. The plurality of phases 108A-108N are selectively controlled based on a load placed on the power supply 104 by the CPU 106 and/or any other components receiving supply signals from the power supply 104. In at least some examples, the multi-phase controller 110 is coupled to, and configured to receive instructions from, the CPU 106 to control at least some of the of the plurality of phases 108A-108N. Each of the plurality of phases 108A-108N is, for example, a power regulator. The power supply 104 further includes a telemetry system 112. The telemetry system 112, in at least some examples, includes an analog-to-digital converter (ADC) 114, and a core 116. In some examples, the telemetry system 112 further includes a plurality of ADCs and each ADC, including the ADC 114, of the telemetry system may have one or more channels. The ADC 114 is configured to receive an analog signal representative of a condition of at least one of the phases 108A-108N and convert that analog signal to a digital signal. The ADC 114 then provides that digital signal to the core 116 for further processing. The analog signal representative of the condition of at least one of the phases 108A-108N may be received from any suitable component or sensor (not shown), the scope of which is not limited herein.

The core 116 is configured to receive the digital signal output by the ADC 114 and generate telemetry data based at least partially on the digital signal. The generation of the telemetry data is at least partially controlled, in some examples, by configuration information received from the CPU 106. In other examples, the core 116 is programmed with default telemetry data generation operations that may be modified by the CPU 106. Alternatively, the configuration information may be received from another device (not shown) capable of logical operations and/or processing. For example, the configuration information may be received from a device (not shown), other than the CPU 106, that implements a state machine to determine and output the configuration information. In at least one example, the core 116 receives configuration information from the CPU 106 that indicates a desired type of telemetry data, a desired format for the telemetry data, etc. Based on the configuration information received from the CPU 106, the core 116 generates a time-multiplexed sequence of operations to generate the telemetry data requested by the CPU 106 in the format also requested by the CPU 106. In other examples, at least some of the configuration information is default telemetry data generation configuration information stored within the core 116 without first being received from the CPU 106.

In at least some examples, the core 116 includes a storage element 118, a telemetry sequencer 120, and a co-processor

122. The storage element 118 may be any suitable device(s) capable of storing data, such as random-access memory (RAM), including static RAM (SRAM), one or more registers, etc. The telemetry sequencer 120, in at least some examples, generates telemetry data based on data received from the ADC 114, data stored in the storage element 118, and/or data stored in local storage (not shown) of the telemetry sequencer 120. The telemetry sequencer 120, in at least one example, implements a digital state machine that generates the telemetry data. The state machine, in at least some examples, implements operations shown and discussed in greater detail with respect to FIG. 4 of the present disclosure to provide at least some of the functionality of the present disclosure. The digital state machine, in at least some examples, provides advantages over other types of processing, such as a general purpose processor, a CPU, or other forms of processing. For example, a CPU may be prohibitively slow in generating telemetry data when multiple data formats are involved. As an example, an exemplary or general purpose CPU may take approximately 50-60 clock cycles to perform a single multiplication between two operands in single precision format. For example, for a series of actions for generating telemetry data that includes multiple (e.g., 10-15) data format conversions and multiple (e.g., 10-15) operations, the CPU may take a prohibitively long time to generate a result. In contrast, the digital state machine driven telemetry system of the present disclosure may perform approximately 10 operations in a total of approximately 10-20 clock cycles. Accordingly, in at least some examples the telemetry sequencer 120 implements the digital state machine and performs the actions of the method 400 of FIG. 4 without the use of a CPU, with an exception of, in some examples, receiving configuration information (e.g., a type and/or format of telemetry data to generate, a series of actions to perform, operations, operands, and/or an intermediate output point) from a CPU and/or providing an intermediate and/or final output to a CPU. For example, in at least some implementations the telemetry sequencer 120 does not utilize a CPU in the generation of telemetry data according to the telemetry data generation process of the present disclosure.

In at least one example, the local storage may be a register that stores a register file containing data. For example, the telemetry sequencer 120 may include a register (not shown) implemented as the local storage. The telemetry sequencer 120 may further include a telemetry engine (not shown) that implements the state machine to generate the telemetry data. The co-processor 122, in some examples, includes functionality and/or circuitry for performing one or more mathematical calculations. For example, in at least some implementations the co-processor 122 is, or includes, an arithmetic logic unit (ALU). For example, in various implementations the co-processor 122 includes any one or more of an adder, a multiplier, a divider, data filter(s), data format converter(s), etc. The components of the co-processor 122, in at least some examples, may be hardware circuits optimized for performing a particular task. For example, the adder is optimized for performing addition or subtraction operations, the multiplier is optimized for performing multiplication operations, etc. At least some components of the co-processor 122 may be shared between or among the hardware circuits of the co-processor 122.

To generate the telemetry data, the telemetry sequencer 120 loads operations and operand into the local storage and schedules the operations for execution by the co-processor 122. For example, based on the digital signal received from the ADC 114 and the configuration information received from the CPU 106, the telemetry sequencer 120 loads a series of actions into the local storage. Loading the series of actions, in at least some examples, includes identifying operations included in the series of actions and scheduling the operations in telemetry sequence slots for sequential execution by the co-processor 122.

After loading the series of actions, the telemetry sequencer 120 loads operands of the series of actions into the local storage. The operands include any one or more of the digital signals received from the ADC 114, data stored in the storage element 118, data received from the CPU 106, and/or data stored in the local storage. For example, the telemetry sequencer 120 may store a listing of operations and/or at least some operands associated with the series of actions to generate telemetry data in the local storage of the telemetry sequencer 120 based on the configuration information received from the CPU 106. In another example, the telemetry sequencer 120 may store a listing of operations and/or at least some operands associated with the series of actions to generate telemetry data in the storage element 118. The listing of operations and/or at least some operands associated with a series of actions stored in the storage element 118 may provide a default operation of the telemetry sequencer 120 in the absence of receipt of specific configuration information from the CPU 106. When the telemetry sequencer 120 receives configuration information from the CPU 106 requesting telemetry data for which the series of actions is stored in the local storage of the telemetry sequencer 120, the telemetry sequencer accesses the local storage to load operations of the series of actions into telemetry sequence slots. In other examples, the listing of operations and/or at least some operands associated with the series of actions to generate telemetry data are stored in the storage element 118 and loaded to the telemetry sequence slots from the storage element 118 by the telemetry sequencer 120.

In at least some examples, the telemetry sequencer 120 loads data to the telemetry sequence slots in a pipelined manner. For example, while operations associated with a first series of actions to generate first telemetry data are being executed, in at least some examples the telemetry sequencer 120 loads the telemetry sequence slots with operations and/or operands associated with a second series of actions to generate second telemetry data. This pipelined processing, in at least some examples, optimizes performance of the core 116 by reducing an amount of time consumed to generate telemetry data. For example, the pipelining enables telemetry data to be generated by the core 116 for each telemetry sequence slot as opposed to alternating between telemetry data being generated in a telemetry sequence slot and a new series of actions being loaded in a next telemetry sequence slot.

In at least some examples, generated telemetry data may be stored by the telemetry sequencer 120 in the storage element 118 or the local storage of the telemetry sequencer 120 and reused as an operand for determining additional telemetry data. For example, telemetry data indicating output current in the PMBUS format may be stored and reused as an operand in determining output current in another, different format, such as the SVID format. In this way, redundant processing common to both telemetry formats is reduced and the same hardware that determines the output current in the PMUS format may also determine the output current in the SVID format. This reuse of hardware reduces a physical size of the core 116 when compared to telemetry systems that utilize hardware solutions specifically tailored for each type of telemetry data and/or format that will be output.

The telemetry sequencer 120, in at least some examples, passes a pair of operands and an operation to the co-processor 122 for processing. The providing of a operands and operations to the co-processor 122, in at least some examples, is referred to as driving the co-processor 122. For example, the telemetry sequencer 120 drives the co-processor 122 to generate an output by providing a pair of operands and an operation to be performed to the co-processor 122. The co-processor 122 then provides an output back to the telemetry sequencer 120 which either stores the output or provides the output back to the co-processor 122 as another operand for processing. For example, after scheduling a series of actions into the telemetry sequence slots, the telemetry sequencer 120 executes the operation with assistance from the co-processor 122. For example, for each operation of the series of actions, the telemetry sequencer 120 passes the operands and an identification of a type of operation to be performed to the co-processor 122. The co-processor 122 then performs the identified operation using the received operands and returns a result to the telemetry sequencer 120. The telemetry sequencer 120 then stores the result in the local storage or storage element 118, reports the result (such as to the CPU 106), or provides the result back to the co-processor 122 with another operand and identification of another operation for execution by the co-processor 122. In at least some examples, the co-processor 122 is any device capable of performing arithmetic operations, including at least addition, subtraction, division, and multiplication. In some examples, the co-processor 122 is a collection of hardware solutions that perform the operations. For example, the co-processor 122 may include a hardware adder, a hardware multiplier, etc. In other examples, the co-processor 122 may include a programmable element that performs at least some of the operations discussed herein. For example, the co-processor 122 may be an arithmetic logic unit (ALU), a field programmable gate array (FPGA), and/or any other structure that has a capability of performing the arithmetic operations or other operations attributed to the co-processor 122 and discussed herein. In at least some examples, the co-processor 122 includes further functionality, implemented through hardware or software, such as format conversion and/or data filtering.

In at least some examples, the telemetry sequencer 120 implements a series of actions for generating telemetry data by performing a sequence of operations with each operation accepting two operands as input. Performing the sequence of operations, in some examples, includes passing the operands to the co-processor 122 for execution by the co-processor 122 and receipt of a result from the co-processor 122. In some examples, telemetry data may be desired (e.g., as indicated in the confirmation information) in multiple formats. Alternatively, or additionally, in some examples a result of an operation, that is not a result of the full series of actions being implemented by the telemetry sequencer 120, may be desired for use in determining other telemetry data. In such examples, the series of actions may be tapped between operations. For example, for a series of actions for generating telemetry data that includes nine operations to generate the telemetry data, in at least some examples the series of actions may be tapped to generate one or more intermediate outputs prior to the ninth operation of the series of actions. For example, a series of actions of nine operations and ten operands may generate telemetry data indicating output current in a first format, such as the SVID format. However, by tapping the series of actions after the sixth operation (or some operation other than the last operation), telemetry data indicating output current in another, different, format, such as the PMBUS format, is generated. In this way, as discussed above, telemetry data in two different formats is generated using substantially the same hardware resources and during a same telemetry sequence slot. This tapping of a series of actions prior to all operations of the series of actions being executed enables more efficient processing by reducing redundant operations and determining multiple telemetry formats in a parallel manner (e.g., substantially concurrently).

Figure 2:
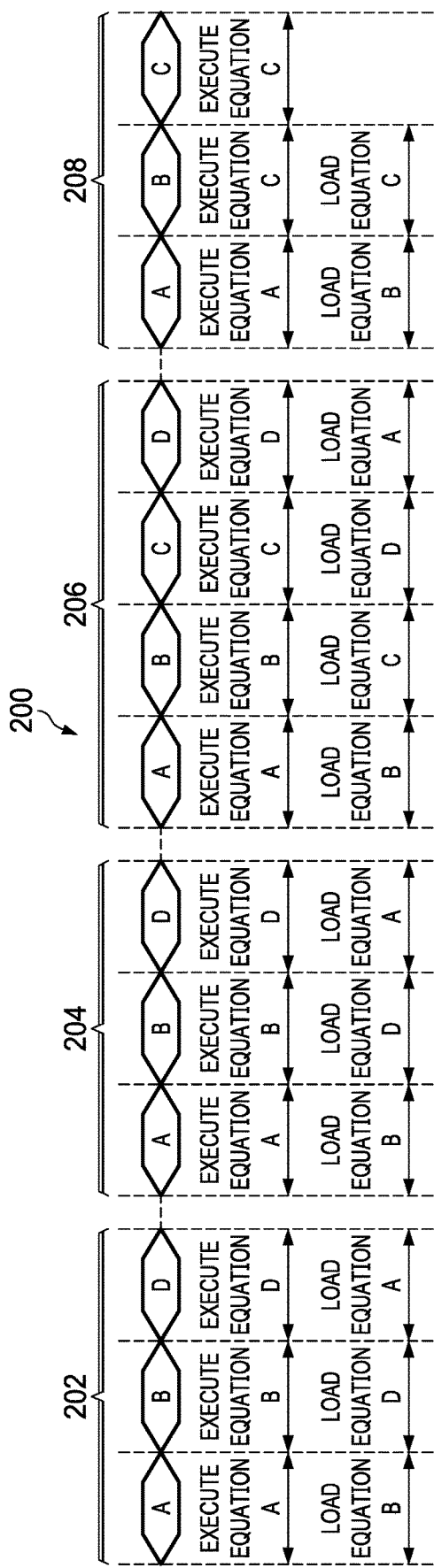
FIG. 2 shows an illustrative diagram of a timing sequence for generation of telemetry data in accordance with various examples.

Turning now to FIG. 2, an illustrative diagram of an example timing sequence 200 for generation of telemetry data is shown. In at least some examples, the timing sequence 200 is generated by the telemetry sequencer 120 and controls an order of operations performed by the co-processor 122, each as discussed above with respect to FIG. 1. For example, when the telemetry sequencer 120 receives a request to generate telemetry data, the telemetry sequencer 120 slots or schedules a series of actions for generating that telemetry data into a telemetry sequence slot. In other examples, the telemetry sequencer 120 is configured to operate at any time the telemetry sequencer 120 is powered on, such as according to a default or preprogrammed telemetry data generation process or schedule. In such an example, when the telemetry sequencer 120 receives a request to generate telemetry data, the telemetry sequencer 120 outputs the requested telemetry data after the telemetry data is generated according to the default or preprogrammed telemetry data generation process or schedule. Series of actions scheduled in the telemetry sequence slots are executed sequentially by the telemetry sequencer 120, in at least some examples, with the help of the co-processor 122. In some examples, certain series of actions may be repeated at greater frequency in the telemetry sequence slots than other series of actions. For example, telemetry data that is needed to remain more current, is of greater importance, is needed in a faster manner, etc. may be scheduled in the telemetry sequence slots more frequently. Conversely, telemetry data that is not needed as rapidly, or is of lesser importance, may be scheduled in the telemetry slots more infrequently. Furthermore, certain telemetry data that is capable of being generated but is not desired by a customer, either generally or at a particular time (e.g., such as during system startup) may not be scheduled in the telemetry sequence slot to prevent unnecessary processing. This is an improvement over at least some examples of telemetry systems that utilize hardware specific solutions for generating telemetry data. For example, at least some of these hardware specific solutions generate telemetry data in a sequential manner, moving from one telemetry parameter to another telemetry parameter until all telemetry data is generated and then beginning again. This wastes processing capacity and power in generating telemetry data that is not of interest to a customer and does not include the flexibility to change frequency of generation of particular telemetry parameters to fit particular implementations.

As shown in FIG. 2, the telemetry sequence slots are scheduled in a pipelined manner. For example, prior to the telemetry sequencer 120 executing series of actions A, the telemetry sequencer 120 loads an operation sequence and operands for implementing series of actions A into the telemetry sequence slots. While executing series of actions A, the telemetry sequencer 120 loads an operation sequence and operands for implementing series of actions B. The above repeats, with an operation sequence and operands for implementing a series of actions in a next telemetry sequence slot being loaded while a series of actions of a current telemetry sequence slot is being executed. As further shown by FIG. 2, the scheduling is dynamic or configurable. For example, during first and second cycles of operation (202 and 204, respectively), telemetry data corresponding to series of actions C is not of interest and therefore the series of actions is not scheduled in a telemetry sequence slot for execution by the co-processor 122. However, beginning with the third cycle of operation 206, the telemetry data corresponding to series of actions C becomes of interest and the series of actions is scheduled in a telemetry sequence slot for execution by the co-processor 122. Further, while the telemetry data corresponding to series of actions D is of interest for the first through third cycles of operation 202-206, the telemetry data corresponding to series of actions D becomes no longer of interest for any desired period of time beginning with the fourth cycle of operation 208. Accordingly, series of actions D is no longer scheduled in a telemetry sequence slot beginning with the fourth cycle of operation 208 and continuing until the telemetry data corresponding to series of actions D again becomes of interest. While the series of actions A, B, C, and D are illustrated with respect to FIG. 2, in various examples any number of series of actions may be scheduled and executed in a cycle of operations. Additionally, a series of actions may be scheduled and executed more than once in a single cycle of operation.

Figure 3:
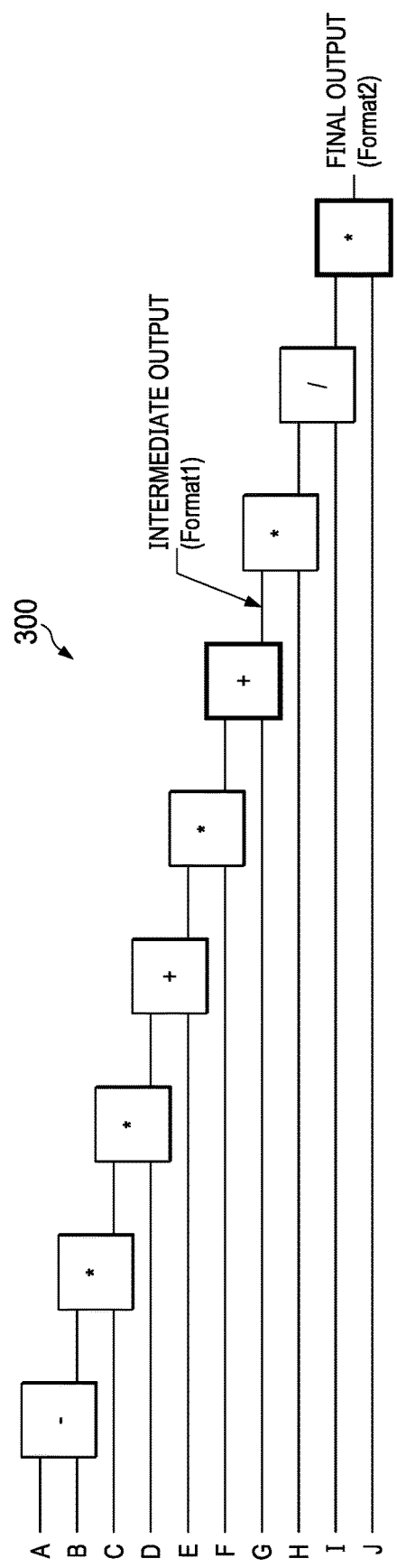
FIG. 3 shows an illustrative diagram of an example sequence of operations for generation of telemetry data in accordance with various examples.

Turning now to FIG. 3, an illustrative diagram of an example sequence 300 of operations for generation of telemetry data is shown. In at least some examples, the sequence 300 is generated by the telemetry sequencer 120, as discussed above with respect to FIG. 1. For example, based on configuration information received by the telemetry sequencer 120, or a default operation sequence, the telemetry sequencer 120 determines operations and operands corresponding to a telemetry parameter. The telemetry sequencer 120 loads these operations and operands into telemetry sequence slots. In at least some examples, these operations and operands are loaded by the telemetry sequencer 120 to the telemetry sequence slots sequentially. The telemetry sequencer 120 then executes the operations shown in the sequence 300 by passing a pair of operands (and in some examples, a data type of at least one of the operands) and an operation to the co-processor 122 for processing by the co-processor 122. For the purposes of illustration, an example of determining output current will be used to describe FIG. 3. However, FIG. 3 and the present disclosure are not so limited, and the teachings of FIG. 3 and the present disclosure apply to a plurality of series of actions and a plurality of telemetry parameters. Additionally, at least some examples of FIG. 3 correspond to one telemetry sequence slot of the timing sequence 200 of FIG. 2. For example, the operations illustrated in the sequence 300 would be performed by the telemetry sequencer 120 by passing operands and operation identifiers to the co-processor 122 in one telemetry sequence slot (e.g., as one of series of actions A, series of actions B, series of actions C, or series of actions D, shown in FIG. 2). Further, the operations and operands of the sequence 300 would be loaded into a telemetry sequence slot by the telemetry sequencer 120 during a telemetry sequence slot that is sequentially one prior to the telemetry sequence slot in which the sequence 300 will be executed by the telemetry sequencer 120.

In at least one example, output current for a particular device may be determined in a first format according to a series of actions IOUT_1=(RawData1−RawData2)*NumberOfPhasesOfPowerConverter*Coefficient1* Coefficient2+Coefficient3. Output current for the device may then be determined in a second format according to a series of actions IOUT_2=IOUT_1*Coefficient4/Coefficient5* Coefficient 6.

For the selection of operations and operands, the above series of actions can be assigned operand identifiers such that IOUT_1=I1, I1=((A-B)*C*D*E)+F, IOUT_2=I2, and I2=I1*G/H*I. In the above, A=RawData1, B=RawData2, C=NumberOfPhasesOfPowerConverter, D=Coefficient1, E=Coefficient2, and F=Coefficient3. Additionally, G= Coefficient4, H=Coefficient5, and I=Coefficient6. In at least some examples, each of the coefficients may be fixed or variable coefficients. As shown in FIG. 3, the telemetry sequencer 120 loads the operations and operands in sequence to implement the above series of actions. For example, the series of actions for determining IOUT_2 includes eight operations, the first five of which are sequentially shared in common with the series of actions for determining IOUT_1. Accordingly, an output of the fifth operation for determining IOUT_2 is IOUT_1. By generating IOUT_1 while also generating IOUT_2, redundant processing (e.g., of the first five operations) is prevented. Additionally, substantially the same hardware is used for generating IOUT_2 and IOUT_1, reducing space when compared to a hardware specific solution utilizing hardware specific to generating IOUT_2 and separate hardware specific to generating IOUT_1.

While eight operations are shown in FIG. 3, in various examples any suitable number of series of actions may be loaded based on system limitations and design tradeoffs. For example, when most series of actions will be X operations or fewer, where X is any non-zero integer, a system may be designed to support a maximum of X operations for a single series of actions. In at least some examples, this may optimize a size of the system (e.g., by preventing the consumption of additional space to support additional operations that will be infrequently used). When more than X operations are required to determine a particular telemetry parameter, in at least one example the output of one series of actions containing X operations may be used as an input (e.g., an operand) to another series of actions containing X or fewer operations. In at least one example of the system of the present disclosure, X is 9.

As another example, output current of a device may be determined in a PMBUS format according to a series of actions IMON_PMBUS=(((V$_{IOUT}$−V$_{AMP\_OFFSET}$)*Gain−V$_{REF}$)*(½^ADC_resolution)/R$_{SENSE}$)+I$_{CHANNEL\_OFFSET}$. In the foregoing series of actions, V$_{IOUT}$ is a signal having a voltage that is representative of the output current of the device, V$_{AMP\_OFFSET}$ is a value representative of an amplifier offset of an amplifier that generates V$_{IOUT}$, Gain is a constant gain value, V$_{REF}$ is a reference voltage, ADC_resolution is a resolution of the ADC 114, R$_{SENSE}$ is a value of resistance of a sense resistor and I$_{CHANNEL\_OFFSET}$ is an offset value for a channel of the ADC 114 performing measurements related to the IMON_PMBUS determination. Output current for the device may then be determined in a SVID format according to a series of actions IMON_SVID=(IMON_PMBUS)*((1/ICCMAX)*0x7FFF)). In the foregoing series of actions, ICCMAX is a maximum current that may be sourced to the device and 0x7FFF is a constant.

For the selection of operations and operands, the above series of actions can be assigned operand identifiers such that IMON_PMBUS=I1, I1=A-B*C-D*E/F+G, IMON_SVID=I2, and I2=I1*H*I. In the above, A=V$_{IOUT}$, B=$V_{AMP\_OFFSET}$, C=Gain, D=$V_{REF}$, E=1.92/2^ADC_resolution*200, F=$R_{SENSE}$, and G=$I_{CHANNEL\_OFFSET}$. Additionally, H=1/ICCMAX, I=0x7FFF. As shown in FIG. 3, the telemetry sequencer 120 loads the processor 122 with the operations in sequence and the operands to implement the above series of actions. For example, the series of actions for determining IMON_SVID includes eight operations, the first six of which are sequentially shared in common with the series of actions for determining IMON_PMBUS. Accordingly, an output of the sixth operation for determining IMON_SVID is IMON_PMBUS. By generating IMON_PMBUS while also generating IMON_SVID, redundant processing (e.g., of the first six operations) is prevented. Additionally, substantially the same hardware is used for generating IMON_SVID and IMON_PMBUS, reducing space when compared to a hardware specific solution utilizing hardware specific to generating IMON_SVID and separate hardware specific to generating IMON_PMBUS.

As another example, output voltage of a device may be determined in a PMBUS format according to a series of actions V_PMBUS=(($V_{OUT}$−$V_{AMP\_OFFSET}$)*Gain−$V_{COMMON\_MODE}$) $V_{CHANNEL\_OFFSET}$. In the foregoing series of actions, $V_{OUT}$ is an output voltage of the device, $V_{AMP\_OFFSET}$ is a value representative of an amplifier offset of an amplifier that generates $V_{OUT}$, Gain is a constant gain value, $V_{COMMON\_MODE}$ is a common mode voltage, and $V_{CHANNEL\_OFFSET}$ is an offset value for a channel of the ADC 114 performing measurements related to the V_PMBUS determination. Output voltage for the device may then be determined in a SVID format according to a series of actions V_SVID=(V_PMBUS)*((1/$V_{MAX}$)*0x7FFF)). In the foregoing series of actions, $V_{MAX}$ is a maximum voltage that may be sourced to the device and 0x7FFF is a constant.

For the selection of operations and operands, the above series of actions can be assigned operand identifiers such that V_PMBUS=V1, V1=A−B*C−D−E, Vv SVID=V2, and V2=V1/F*G. In the above, A=$V_{OUT}$, B=$V_{AMP\_OFFSET}$, C=Gain, D=$V_{COMMON\_MODE}$, and E=$V_{CHANNEL\_OFFSET}$. Additionally, F=1/$V_{MAX}$, G=0x7FFF. As shown in FIG. 3, the telemetry sequencer 120 loads the processor 122 with the operations in sequence and the operands to implement the above series of actions. For example, the series of actions for determining V_SVID includes six operations, the first four of which are sequentially shared in common with the series of actions for determining V_PMBUS. Accordingly, an output of the fourth operation for determining V_SVID is V_PMBUS. By generating V_PMBUS while also generating V_SVID, redundant processing (e.g., of the first four operations) is prevented. Additionally, substantially the same hardware is used for generating V_SVID and V_PMBUS, reducing space when compared to a hardware specific solution utilizing hardware specific to generating V_SVID and separate hardware specific to generating V_PMBUS.

Generally, in at least some examples a series of actions for generating a telemetry parameter and/or telemetry data in a particular format may be split into a sequence of cascaded operations programmable by a customer or user via the configuration information, or pre-programmed at a time of system manufacturing. For example, each telemetry parameter (which may sometimes be referred to as a telemetry channel or simply a channel) may have a corresponding memory location that stores configuration settings, including at least a series of actions and, in some examples, at least some operands, for that telemetry parameter. In some examples, the memory location is the storage element 118, while in other examples the memory location is another device capable of storing data. In at least some examples, the configuration settings are transferred (e.g., copied) from the memory location to the storage element of the telemetry sequencer 120 in advance of the telemetry sequencer 120 generating telemetry data according to the configuration settings. To generate a specific telemetry parameter, the corresponding memory location is accessed by the telemetry sequencer 120 to acquire the operations and/or at least some operands associated with the series of actions for determining the telemetry parameter. The operations and/or at least some operands are subsequently loaded, along with data output by the ADC 114 (which may have been previously stored), by the telemetry sequencer 120 into telemetry sequence slots for execution of the series of actions.

Additionally, while one tap or intermediate output is shown in FIG. 3, and that tap point is between operations six and seven, in other examples any number of tap points may exist and before or after any desired operation of a series of actions. For example, a series of actions may have no tap points, 1 tap point, 2 tap points, 3 tap points, etc. based on requested telemetry parameters and/or telemetry formats.

Figure 4:
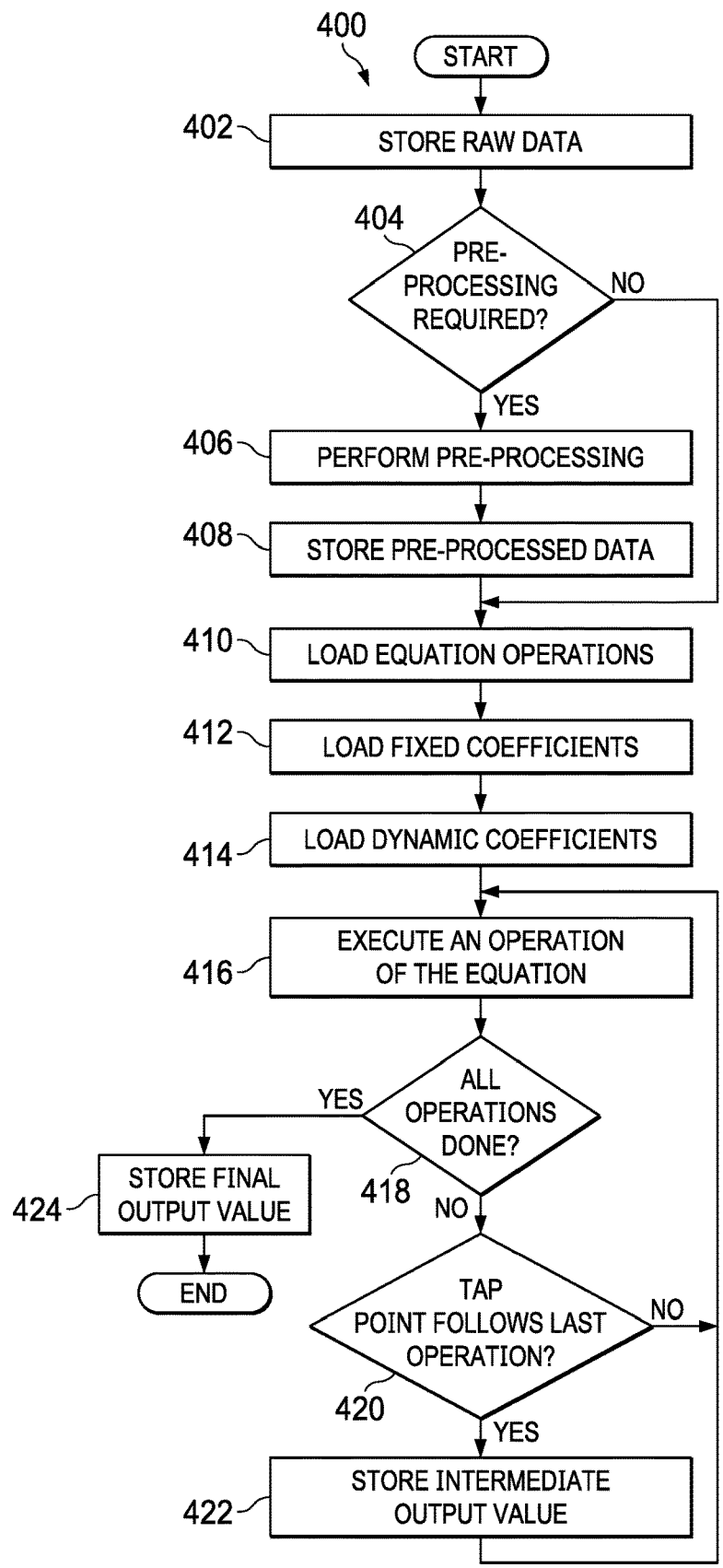
FIG. 4 shows a flowchart of an illustrative method of telemetry data generation in accordance with various examples.

Turning now to FIG. 4, an illustrative flowchart of a method 400 of telemetry data generation is shown. In at least some examples, the method 400 is implemented at least partially by the core 116 of FIG. 1 and reference is made to elements of FIG. 1 in describing the method 400. The method 400, in at least some examples, is a method for generating telemetry data via a configurable or programmable telemetry system that does not utilize hardware specific to each telemetry parameter or telemetry format supported. Instead, the telemetry system is programmable according to a series of actions for generating a requested telemetry parameter and/or telemetry format. In at least some examples, this lack of reliance on a hardware specific solution for telemetry data generation, and further lack of use of a CPU core for generating telemetry data, results in faster and more flexible operation according to the method 400. For example, the method 400 enables generation of telemetry data in about 300-400 nanoseconds in a 100 megahertz system (e.g., generation of telemetry data in about 30-40 clock cycles). This enables faster generation of telemetry data than possible with at least some examples of CPU generation of telemetry data. Further, the method 400 facilitates the definition of additional telemetry parameters or formats, or modification of existing telemetry parameters or formats, after manufacturing of a system implementing the method 400, improving over the hardware specific solutions discussed elsewhere herein.

At operation 402, raw data is stored. In at least some examples, the raw data is sensor data (e.g., data resulting from sensor measurements). The sensor data is, in some examples, a measurement output in a digital format by the ADC 114. In at least some examples, the measurement is of a condition of a circuit, such as a power converter. In some examples, the power converter is a component of a multi-phase power supply. In other examples, the circuit is any circuit being monitored and for which telemetry data is requested. The data is stored, in some examples, in a short-term (e.g., volatile) memory such as SRAM, a register, a non-volatile memory, or any other suitable storage element or location that is later accessible for determining and/or reporting telemetry data.

At operation 404, a determination is made of whether pre-processing of the sensor data is required. When pre-processing is required, the method 400 proceeds to operation 406. At operation 406, pre-processing is performed. The pre-processing may include determining a finite impulse response (FIR) of the sensor data, determining an average of the sensor data, determining an offset for the sensor data, etc. At operation 408, the pre-processed data is stored. The pre-processed data may be stored in any suitable manner and in any suitable location, such as discussed at operation 402 with respect to the sensor data.

Returning now to operation 404, when pre-processing is not required, the method 400 proceeds to operation 410. At operation 410, a series of actions is loaded. In at least some examples, the series of actions is loaded by the telemetry sequencer 120 into telemetry sequence slots as a series of operations whose operands are loaded according to subsequent operations. The series of actions, in some examples, is accessed from memory and defines one or more operations and operands for generating a particular telemetry parameter and/or telemetry data in a particular format. The telemetry sequence slots, in at least some examples, are stored in a local storage element of the telemetry sequencer 120. In some examples, the series of actions was previously received by the core 116 from a user via a processor or other device that configures the core 116 and was then stored by the core 116 in the memory. The telemetry sequencer 120 loads the series of actions to the telemetry sequence slots, in some examples, as a cascaded series of operations, where an output of a preceding operation is an input to a following operation until a final result is determined. A final result or output of a series of actions, as used herein, is a value resulting from execution and/or calculation according to a last operation of the series of actions. For example, for series of actions of (A+B)*C=D, D is the final result of the series of actions. An intermediate result or output of a series of actions, as used herein, is a value resulting from execution and/or calculation according to an operation of the series of actions that is not the last operation of the series of actions. For example, for the series of actions (A+B)*C=D, an intermediate result may be a value resulting from the addition of A and B, prior to multiplication of that value by C to determine the final result of the series of actions. In at least some examples, the telemetry sequencer 120 schedules or slots a plurality of series of actions for execution in a pipelined manner, such as discussed elsewhere herein.

At operation 412, fixed coefficients are loaded. In at least some examples, the fixed coefficients are loaded by the telemetry sequencer 120 into the telemetry sequence slots as operands of the series of actions. The fixed coefficients, in some examples, are accessed from memory and are one or more operands for generating the particular telemetry parameter in the particular format defined by the series of actions. In some examples, the fixed coefficients were previously received by the core 116 from the user via the processor or other device that configures the core 116 and were then stored by the core 116 in the memory.

At operation 414, dynamic coefficients are loaded. In at least some examples, the dynamic coefficients are loaded by the telemetry sequencer 120 into the telemetry sequence slots as operands of the series of actions. The dynamic coefficients, in some examples, are the sensor data previously stored at operation 402 and/or the pre-processed data previously stored at operation 408.

At operation 416, an operation of the series of actions is executed. The operation of the series of actions is executed, for example, by the telemetry sequencer 120 with assistance of the co-processor 122. For example, the telemetry sequencer 120 may transmit a pair of operands and an identification of an operation to be performed to the co-processor 122 for processing. The pair of operands and the identification of the operation to be performed are selected, in at least some examples, based on the telemetry sequence slots based on a first in-first out methodology. In various examples, the operation may be an arithmetic operation, such as multiplication, division, addition, or subtraction. In other examples, the operation may be any suitable operation for altering, processing (e.g., averaging, filtering, etc.), or otherwise manipulating the fixed coefficients and/or the dynamic coefficients for use in generating the telemetry data defined by the series of actions.

At operation 418, a determination is made of whether all operations of the series of actions have been executed. When all operations of the series of actions have not been executed, the method proceeds to operation 420. At operation 420, a determination is made of whether a tap point follows the last executed operation. When a tap point follows the last executed operation, the method proceeds to operation 422. At operation 422, an output value or result of the last executed operation (e.g., an intermediate output value) is stored. For example, the telemetry sequencer 120 stores the output value of the last executed operation in a memory location for later output to a user, output to another electrical component, or use as an operand in another series of actions for generating telemetry data. Returning now to operation 420, when a tap point does not follow the last executed operation, the method returns to operation 418. Returning now to operation 418, when all operations of the series of actions have been executed, the method proceeds to operation 424. At operation 424, an output value of the series of actions (e.g., a final output value) is stored. The output value of the series of actions is, for example, output value or result of the last executed operation. In at least one example, the telemetry sequencer 120 stores the output value of the series of actions in a memory location for later output to a user, output to another electrical component, or use as an operand in another series of actions for generating telemetry data.

In at least some examples, the method 400 is performed for each telemetry parameter generated by a system implementing the method 400, such as the telemetry system 112. For example, the telemetry system 112 implements a new instance of the method 400 for each telemetry sequence slot of the telemetry system 112 (e.g., as shown above with respect to FIG. 2).

While the operations of the method 400 have been discussed and labeled with numerical reference, in various examples the method 400 includes additional operations that are not recited herein. In some examples any one or more of the operations recited herein include one or more sub-operations (e.g., such as intermediary comparisons, logical operations, output selections such as via a multiplexer, format conversions, etc.). In some examples any one or more of the operations recited herein is omitted. In some examples any one or more of the operations recited herein is performed in an order other than that presented herein (e.g., in a reverse order, substantially simultaneously, overlapping, etc.). Each of these alternatives is intended to fall within the scope of the present disclosure.

In the foregoing discussion, the terms "including" and "comprising" are used in an open-ended fashion, and thus should be interpreted to mean "including, but not limited to . . . ." The term "couple" is used throughout the specification. The term may cover connections, communications, or signal paths that enable a functional relationship consistent with the description of the present disclosure. For example, if device A generates a signal to control device B to perform an action, in a first example device A is coupled to device B, or in a second example device A is coupled to device B through intervening component C if intervening component C does not substantially alter the functional relationship between device A and device B such that device B is controlled by device A via the control signal generated by device A. A device that is "configured to" perform a task or function may be configured (e.g., programmed and/or hardwired) at a time of manufacturing by a manufacturer to perform the function and/or may be configurable (or re-configurable) by a user after manufacturing to perform the function and/or other additional or alternative functions. The configuring may be through firmware and/or software programming of the device, through a construction and/or layout of hardware components and interconnections of the device, or a combination thereof. Furthermore, a circuit or device that is said to include certain components may instead be configured to couple to those components to form the described circuitry or device. For example, a structure described as including one or more semiconductor elements (such as transistors), one or more passive elements (such as resistors capacitors and/or inductors), and/or one or more sources (such as voltage and/or current sources) may instead include only the semiconductor elements within a single physical device (e.g., a semiconductor die and/or integrated circuit (C) package) and may be configured to couple to at least some of the passive elements and/or the sources to form the described structure either at a time of manufacture or after a time of manufacture, for example, by an end-user and/or a third-party.

While certain components are described herein as being of a particular process technology, these components may be exchanged for components of other process technologies that achieve equivalent functionality to that described herein. Circuits described herein may be at least partially reconfigured to include the replaced components to provide desired functionality at least partially similar to functionality available prior to the component replacement. Components illustrated as resistors, unless otherwise stated, are generally representative of any one or more elements coupled in series and/or parallel to provide an amount of impedance represented by the illustrated resistor. Additionally, uses of the phrase "ground voltage potential" in the foregoing discussion are intended to include a chassis ground, an Earth around, a floating ground, a virtual ground, a digital ground, a common ground, and/or any other form of ground connection applicable to, or suitable for, the teachings of the present disclosure. Unless otherwise stated, "about", "approximately", or "substantially" preceding a value means +/−10 percent of the stated value.

The above discussion is meant to be illustrative of the principles and various examples of the present disclosure. Numerous variations and modifications will become apparent to those skilled in the art once the above disclosure is fully appreciated. It is intended that the present disclosure be interpreted to embrace all such variations and modifications.

What is claimed is:

1. A circuit, comprising:
   a storage element;
   a hardware set; and
   a state machine coupled to the storage element and to the hardware set, the state machine configured to:
   obtain configuration information indicating a telemetry data type;
   obtain operations and operands associated with the telemetry data type from the storage element for a series of actions to produce telemetry data;
   transmit at least some of the operations and at least some of the operands to the hardware set, wherein the hardware set is configured to process the at least some of the operations and the at least some of the operands, to produce a first output in a first format and a second output in a second format;
   receive the first output of the series of actions as the telemetry data in the first format from the hardware set; and
   receive the second output of the series of actions as the telemetry data in the second format from the hardware set.

2. The circuit of claim 1, wherein the state machine is further configured to drive the hardware set for telemetry sequence slots, a telemetry sequence slot of the telemetry sequence slots representing a processing slot during which the state machine generates one type of telemetry data in at least one format based at least partially on data received from the hardware set.

3. The circuit of claim 2, wherein the state machine is further configured to transmit the operations and the operands to the hardware set one telemetry sequence slot prior to a telemetry sequence slot during which the hardware set is configured to execute the series of actions defined by the operations and the operands.

4. The circuit of claim 1, wherein the state machine is further configured to:
   receive the series of actions, the operations, at least some of the operands, and a first operation after which to take the first output of the series of actions, from a central processing unit; and
   store the series of actions, the operations, at least some of the operands, and a second operation after which to take an intermediate output of the series of actions in the storage element.

5. The circuit of claim 1, wherein at least one of the operands is a digital signal output of an analog-to-digital converter, where the digital signal output indicates a condition of a second circuit.

6. The circuit of claim 5, wherein the circuit is a multiphase power supply.

7. The circuit of claim 1, wherein the configuration information is first configuration information, the series of actions is a first series of actions, the operands are first operands, and the operations are first operations, and the state machine is further configured to:
   obtain second configuration information indicating a second telemetry data type;
   retrieve second operations and second operands associated with the second telemetry data type for a second series of actions from the storage element;
   program, while the state machine executes the first series of actions, the second operations and the second operands associated with the second telemetry data type into a telemetry sequence slot for execution after the state machine executes the series of actions;
   transmit at least some of the second operations and at least some of the second operands to the hardware set, wherein the hardware set is configured to process the at least some of the second operations and the at least some of the second operands; and
   receive, from a third output of the second series of actions from the hardware set responsive to the at least some of the second operations and the at least some of the second operands.

8. A method comprising:
   receiving sensor data by a state machine;
   loading operations and operands for a series of actions, by the state machine, wherein an operand of the operands comprises the sensor data, and wherein loading the operations and the operands comprises:
loading the operations into a telemetry sequence slot for a hardware set; and
loading the operands into the telemetry sequence slot for the hardware set;
executing the series of actions to produce an output, by the state machine, wherein executing the series of actions comprises passing at least some of the operations and at least some of the operands to the hardware set; and
storing the output as telemetry data in a format by the state machine.

9. The method of claim 8, wherein the output is a first output, the format is a first format, and the method further comprising storing a second output as the telemetry data in a second format, wherein the first output is a result of a last operation of the series of actions and the second output is a result of an operation of the series of actions that is not the last operation of the series of actions.

10. The method of claim 9, wherein the series of actions is a first series of actions, the telemetry data is first telemetry data, the operations are first operations, the operands are first operands, the telemetry sequence slot is a first telemetry sequence slot, and the method further comprising:
loading second operations and second operands for a second series of actions loading the second operations and the second operands comprises:
loading the second operations into a second telemetry sequence slot for the hardware set; and
loading the second operands into the second telemetry sequence slot for the hardware set, wherein at least one of the second operands is the first telemetry data in the first format or the first telemetry data in the second format;
executing the second series of actions to produce a third output that is a result of a last operation of the second series of actions; and
storing the third output as second telemetry data.

11. The method of claim 8, wherein the sensor data is digital sensor data, the method further comprising:
receiving analog sensor data;
converting the analog sensor data to the digital sensor data with an analog-to-digital converter; and
storing the digital sensor data in a memory.

12. The method of claim 11, further comprising instructing the hardware set to pre-process the digital sensor data prior to storing the digital sensor data.

13. The method of claim 8, further comprising receiving configuration information from a central processing unit, wherein the configuration information indicates:
the series of actions;
the operations;
at least some of the operands; and
an operation of the operations after which to take an intermediate output.

14. The method of claim 8, wherein the operations are first operations, the operands are first operands, the series of actions is a first series of actions, the method further comprising loading second operations and second operands associated with a second series of actions while executing the first series of actions.

15. The method of claim 8, wherein the sensor data indicates a condition in a multi-phase power supply of a server system, and wherein the method further comprises modifying a value of an output signal of the multi-phase power supply responsive to the output.

16. The method of claim 8, further comprising loading, by the state machine, a plurality of series of actions into telemetry sequence slots that each contain one series of actions, and wherein the telemetry sequence slots are dynamically reconfigurable to alter their sequence of series of actions.

17. The method of claim 8, wherein a number of the operations, at least some of the operands, or a data type of at least some of the operations is changeable between execution of the series of actions and execution of another series of actions.

18. The method of claim 8, wherein the format is independent of a hardware component that generates the output.

* * * * *